United States Patent [19]
Dorn et al.

[11] Patent Number: 5,804,403
[45] Date of Patent: Sep. 8, 1998

[54] STABLE AQUEOUS REAGENT CONTAINING NAD

[75] Inventors: Allen R. Dorn, Carmel; Catherine J. Hurt, Indianapolis; Edward O. Ganser, Fishers, all of Ind.

[73] Assignee: Boehringer Mannheim Corporation, Indianapolis, Ind.

[21] Appl. No.: 791,920

[22] Filed: Jan. 31, 1997

[51] Int. Cl.$^6$ .............................. C12Q 1/32; C12Q 1/00; G01N 33/48

[52] U.S. Cl. .................. 435/26; 435/4; 436/63; 536/1.11; 536/124

[58] Field of Search ............................ 435/26, 4; 436/63; 536/1.11, 124

[56] References Cited

U.S. PATENT DOCUMENTS

| | | | |
|---|---|---|---|
| 3,948,731 | 4/1976 | Weaver | 435/29 |
| 4,769,321 | 9/1988 | Self | 435/29 |
| 5,254,636 | 10/1993 | Kwak et al. | 435/29 |
| 5,374,562 | 12/1994 | Simon | 435/29 |
| 5,407,958 | 4/1995 | Heath et al. | 435/29 |
| 5,449,522 | 9/1995 | Hill | 435/29 |
| 5,580,566 | 12/1996 | Syverson et al. | 435/29 |
| 5,629,081 | 5/1997 | Richards et al. | 435/29 |

OTHER PUBLICATIONS

Derwent WPI Abstract of JP 59–82398 (May 12, 1984), 1 page total.

Partial English translation of JP 59–82398 (May 12, 1984), Translated by John F. Bukacek, pp. 1–8.

Nichols et al., "Multi–site evaluation of Boehringer Mannheim liquid–stable enzymatic ethanol reagent" *Clinical Chemistry* (1995) 41(6):S125 (Abstract 408).

Nichols et al., "Multicenter evaluation of Boehringer Mannheim liquid–stable enzymatic ethanol reagents" Description of the poster presentation made available at the 47th Annual Meeting of the American Association for Clinical Chemistry, Inc., Anaheim, California, Jul. 16–20, 1995, 8 pages total.

Dialog®, File 398 "CHEMSEARCH" printout of Suttocide A Entry. 1 page total, (1997).

Excerpt from "Suttocide A" brochure from Sutton Laboratories. 5 pages total, (1997).

*Primary Examiner*—Louise N. Leary
*Attorney, Agent, or Firm*—Morrison & Foerster LPP

[57] ABSTRACT

A stable aqueous NAD reagent useful in the measurement of analytes in biological fluids, particularly ethanol and lactate. For the determination of alcohol, the reagent contains alcohol dehydrogenase, pyrazole, NAD, SUTTOCIDE A and an aliphatic, zwitterionic buffer having a secondary or tertiary amine group. Preferred buffers are TAPSO, AMPSO, POPSO, TAPS and DIPSO. For the determination of lactate, the reagent contains lactate dehydrogenase, pyrazole, NAD, SUTTOCIDE A and an aliphatic, zwitterionic buffer having a secondary or tertiary amine group.

8 Claims, No Drawings

STABLE AQUEOUS REAGENT CONTAINING NAD

DESCRIPTION OF THE INVENTION

This application claims priority benefit of provisional patent application 60/011,071, filed Feb. 2, 1996. The content of said application is hereby incorporated by reference herein in its entirety.

The present invention provides a stable liquid reagent useful in the measurement of analytes in biological fluids. In particular, the invention provides a stable liquid reagent useful in measurements in which nicotinamide adenine dinucleotide (NAD) is used as a coenzyme and in which the reduction of NAD is relied upon. The invention is especially useful in the measurement of ethanol using the enzyme alcohol dehydrogenase (ADH) and in the measurement of lactate using the enzyme lactate dehydrogenase (LDH). The measurement technique used for measuring ethanol employs the following reaction scheme:

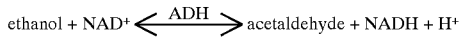

Ethanol and NAD are converted to acetaldehyde and NADH by ADH. The NADH formed during the reaction is measured photometrically and is directly proportional to the ethanol concentration in the sample.

It has been discovered that, by incorporating certain aliphatic, zwitterionic buffers having a secondary or tertiary amine group, in an aqueous solution of alcohol dehydrogenase and NAD, that a stable liquid reagent is formed useful for measurement of ethanol in biological samples. The liquid reagent containing the NAD appears to be stable indefinitely, or at least for a number of years, especially if stored under refrigeration when not in use. Prior art reagents required lyophilization to impart stability to them NAD or the addition of polyols to impart stability to the alcohol dehydrogenase.

Highly preferred buffers are 3-[N-tris-(hydroxymethyl) methylamino]-2-hydroxy-propanesulfonic acid (TAPSO) and 3-[dimethyl (hydroxymethyl) methylamino]-2-hydroxy-propanesulfonic acid (AMPSO). Also suitable for use in the present invention are piperazine-N,N'-bis(2-hydroxypropanesulfonic acid) (POPSO), 3-[N-tris-(hydroxymethyl) methylamino]-propanesulfonic acid (TAPS), and 3-[N,N-bis (hydroxyethyl) amino]-2-hydroxy-propanesulfonic acid (DIPSO). AMPSO, TAPSO and TAPS are secondary amines and DIPSO is a tertiary amine. Buffers found to be less effective and generally unsuitable for use in the present invention for stabilizing NAD include HEPPSO, HEPPS, TRICINE, BICINE, CHES, TRIS, diethanolamine, triethanolamine, morpholine, 3-diethylamino-1,2-propanediol, diisopropanolamine, triisopropanolamine, N-ethyldiethanolamine, N,N-bis(2-hydroxyethyl)-amino)-2-propanediol, N,N-diethanolamine, 1-dimethylamino-2-propanol, 3-dimethylamino-1-propanol, 2-propylaminoethanol, 3-dimethylamino-1,2-propanediol, and N,N-dimethylethanolamine. When a buffer is ineffective, the reagent solution is characterized by a high background absorbance at 340 nm due to the reduction of NAD upon standing.

It has also been discovered that the inclusion of SUTTOCIDE A sodium hydroxymethylglycinate, sold under the trademark (GAF Chemicals Corp.) in an aqueous solution of alcohol dehydrogenase and NAD further increased the stability of the reagent composition. SUTTOCIDE A is advantageous in that it is environmentally desirable and permits a reduction in the amount of environmentally undesirable preservatives such as sodium azide otherwise considered necessary.

A preferred pH is 7.9, but any pH below about pH 8 can be used depending upon specific assay requirements and requirements of specific enzymes and other reagent components. The amounts of ADH, NAD, pyrazole and buffer used may also be varied and optimized by one skilled in the art according to specific assay parameters and reagent requirements. The amount of SUTTOCIDE disclosed, 0.1%, is a preferred amount; however, that concentration can also be varied by the skilled artisan. Generally, the preferred range will be between about 0.05% and 0.2% by weight. Lower amounts of SUTTOCIDE A will be less effective in retarding the growth of bacteria, yeasts and molds, while higher amounts will result in reduction of NAD and a resulting increase in background absorbance of the reagent. SUTTOCIDE A also is a zwitterionic compound having an aliphatic, secondary amine structure, and antimicrobials having aromatic ring structures or reactive groups were found not to be effective with the present invention.

Other stabilizers and preservatives known to those skilled in the art may also be included in the composition but are not required in the practice of the present invention. Examples of such compounds include sodium azide, EGTA, and bovine serum albumin (BSA).

It has been further discovered that the present invention is useful in a variety of assays where a stable liquid reagent containing NAD is desirable, e.g., an assay for lactate using the enzyme LDH. Further utility is predicted in assay methods and reagents for other serum analytes such as LDH and LD1.

EMBODIMENTS

In a preferred embodiment, a stable aqueous reagent for measuring serum ethanol (R2) was formulated to have the following composition:

| | |
|---|---|
| Yeast ADH | 150 KU/liter |
| Pyrazole | 40 mM |
| NAD | 15 mM |
| TAPSO | 100 mM |
| SUTTOCIDE A | 3.9 mM |
| EGTA | 10 mM |
| Sodium azide | 14.6 mM |
| BSA | 1% |
| pH | 7.9 |

A second aqueous reagent (R1) was formulated to have the following composition:

| | |
|---|---|
| Tris base | 500 mM |
| Tris HCl | 250 mM |
| SUTTOCIDE A | 3.9 mM |
| Sodium azide | 14.6 mM |
| pH | 7.9 |

Ethanol measurements were made with an HITACHI 717 analyzer (Boehringer Mannheim Corp., Indianapolis). The primary wavelength used was 340 nm and the secondary wavelength was 700 nm. The analyzer dispensed 10 µl of sample into a cuvette incubated in a waterbath at 37° C. Then 125 µl of R1 was added to the sample, mixed and allowed to incubate for 5 minutes, after which time 125 µl of R2 was added and mixed. The rate of absorbance increase at 340 nm was measured over the time period of 89.09 sec to 255.27 sec following the addition of R2. The absorbance rate at 340 nm is directly proportional to the ethanol concentration in the sample.

In one particular assay, the sample assayed was quality control serum containing a target, or theoretical, level of ethanol of 188 mg/dl. When the quality control material was assayed using the reagents and method described above, absorbance measurements taken at 340 nm were compared to those of a standard solution containing 100 mg/dl ethanol and found to be equivalent to an ethanol concentration of 181.2 mg/dl.

In another embodiment, a stable aqueous reagent for measuring serum lactate (R2) was formulated to have the following composition:

| | |
|---|---|
| LDH | 50 U/ml |
| Sodium oxalate | 60 mM |
| NAD | 15 mM |
| TAPSO | 0.1 M |
| SUTTOCIDE A | 0.1% |
| EGTA | 10 mM |
| Sodium azide | 0.095% |
| pH | 7.9 |

A second aqueous reagent (R1) was formulated to have the following composition:

| | |
|---|---|
| 2-amino-2-methyl-1-propanol | 0.75 M |
| SUTTOCIDE A | 0.05% |
| Sodium azide | 0.0475% |
| pH | 9 |

Lactate measurements were made with an HITACHI 717 analyzer. The primary wavelength used was 340 nm and the secondary wavelength was 700 nm. The analyzer dispensed 10 $\mu$l of sample into a cuvette incubated in a waterbath at 37° C. Then 125 $\mu$l of R1 was added to the sample, mixed and allowed to incubate for 5 minutes, after which time 125 $\mu$l of R2 was added and mixed. The rate of absorbance increase at 340 nm was measured over a 25 second time period following the addition of R2. The absorbance rate at 340 nm is directly proportional to the lactate concentration in the sample.

In one particular experiment, the sample assayed contained a target level of lactate of 100 mg/dl. When the sample was assayed using the reagents and method described above, absorbance measurements taken at 340 nm were as follows:

| Sample | $A_{25\ sec}$ | $A_{30\ sec}$ | $A_{35\ sec}$ | $A_{40\ sec}$ | $A_{45\ sec}$ | $A_{50\ sec}$ |
|---|---|---|---|---|---|---|
| 60/10 | .3584 | .4944 | .6403 | .7574 | .8446 | .9109 |

What is claimed is:

1. An aqueous reagent composition for measuring ethanol in a biological sample comprising alcohol dehydrogenase, pyrazole, NAD, sodium hydroxymethylglycinate and an aliphatic, zwitterionic buffer having a secondary or tertiary amine group.

2. The composition of claim 1 wherein said buffer is selected from the group consisting of 3-[N-tris-(hydroxymethyl) methylamino]-2-hydroxypropanesulfonic acid (TAPSO), 3-[dimethyl (hydroxymethyl) methylamino]-2-hydroxypropanesulfonic acid (AMPSO), piperazine-N,N'-bis(2-hydroxypropanesulfonic acid) (POPSO), 3-[N-tris-(hydroxymethyl) methylamino]-propanesulfonic acid (TAPS), and 3-[N, N-bis(hydroxyethyl) amino]-2-hydroxypropanesulfonic acid (DIPSO).

3. An aqueous reagent composition for measuring lactate in a biological sample comprising lactate dehydrogenase, pyrazole, NAD, sodium hydroxymethylglycinate and an aliphatic, zwitterionic buffer having a secondary or tertiary amine group.

4. The composition of claim 3 wherein said buffer is selected from the group consisting of 3-[N-tris-(hydroxymethyl) methylamino]-2-hydroxypropanesulfonic acid (TAPSO), 3-[dimethyl (hydroxymethyl) methylamino]-2-hydroxypropanesulfonic acid (AMPSO), piperazine-N,N'-bis(2-hydroxypropanesulfonic acid) (POPSO), 3-[N-tris-(hydroxymethyl) methylamino]-propanesulfonic acid (TAPS), and 3-[N, N-bis(hydroxyethyl) amino]-2-hydroxypropanesulfonic acid (DIPSO).

5. A method for measuring ethanol in a biological sample comprising a. adding to said sample a reagent mixture comprising alcohol dehydrogenase, pyrazole, NAD, sodium hydroxymethylglycinate and an aliphatic, zwitterionic buffer having a secondary or tertiary amine group;

b. measuring the rate of formation of NADH from NAD; and c. comparing the rate measured in step (b) with the rate of formation of NADH in a sample containing a known amount of ethanol.

6. The method of claim 5 wherein said buffer is selected from the group consisting of 3-[N-tris-(hydroxymethyl) methylamino]-2-hydroxypropanesulfonic acid (TAPSO), 3-[dimethyl (hydroxymethyl) methylamino]-2-hydroxypropanesulfonic acid (AMPSO), piperazine-N,N'-bis(2-hydroxypropanesulfonic acid) (POPSO), 3-[N-tris-(hydroxymethyl) methylamino]-propanesulfonic acid (TAPS), and 3-[N, N-bis(hydroxyethyl) amino]-2-hydroxypropanesulfonic acid (DIPSO).

7. A method for measuring lactate in a biological sample comprising a. adding to said sample a reagent mixture comprising lactate dehydrogenase, pyrazole, NAD, sodium hydroxymethylglycinate and an aliphatic, zwitterionic buffer having a secondary or tertiary amine group;

b. measuring the rate of formation of NADH from NAD; and c. comparing the rate measured in step (b) with the rate of formation of NADH in a sample containing a known amount of lactate.

8. The method of claim 7 wherein said buffer is selected from the group consisting of 3-[N-tris-(hydroxymethyl) methylamino]-2-hydroxypropanesulfonic acid (TAPSO), 3-[dimethyl (hydroxymethyl) methylamino]-2-hydroxypropanesulfonic acid (AMPSO), piperazine-N,N'-bis(2-hydroxypropanesulfonic acid) (POPSO), 3-[N-tris-(hydroxymethyl) methylamino]-propanesulfonic acid (TAPS), and 3-[N, N-bis(hydroxyethyl) amino]-2-hydroxypropanesulfonic acid (DIPSO).

* * * * *